(12) United States Patent
Banas et al.

(10) Patent No.: US 6,383,214 B1
(45) Date of Patent: *May 7, 2002

(54) ENCAPSULATED STENT

(75) Inventors: Christopher E. Banas, Mesa; Tarun J. Edwin, Chandler, both of AZ (US)

(73) Assignee: IMPRA, Inc., a subsidiary of C. R. Bard, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/531,833

(22) Filed: Mar. 21, 2000

Related U.S. Application Data

(63) Continuation of application No. 08/401,871, filed on Mar. 10, 1995, now Pat. No. 6,124,523.

(51) Int. Cl.[7] ................................................. A61F 2/06
(52) U.S. Cl. ...................... 623/1.14; 623/1.13; 623/1.2; 623/1.31; 623/1.44
(58) Field of Search ..................... 606/108, 191–200; 623/1.1, 1.13, 1.14, 1.15–1.28, 1.36, 1.3, 1.31, 1.38–1.54, 11.11

(56) References Cited

U.S. PATENT DOCUMENTS 5,735,892 A * 4/1998 Myers et al. ............... 623/1.44
6,124,523 A * 9/2000 Banas et al. ................. 623/11

* cited by examiner

Primary Examiner—Glenn K. Dawson
(74) Attorney, Agent, or Firm—Morrison & Foerster LLP; Todd W. Wight

(57) ABSTRACT

An encapsulated stent having a stent or structural support layer sandwiched between two biocompatible flexible layers. One preferred embodiment has a stent cover which includes a tubular shaped stent that is concentrically retained between two tubular shaped grafts comprised of expanded polytetrafluoroethylene. Another preferred embodiment has a stent graft which includes at least one stent sandwiched between the ends of two tubular shaped grafts wherein at least a portion of the grafts are unsupported by the stent. Still another embodiment includes an articulating stented graft which includes a plurality of stents spaced apart from one another at a predetermined distance wherein each stent is contained between two elongated biocompatible tubular members. The graft/stent/graft assemblies all have inseparable layers.

3 Claims, 7 Drawing Sheets

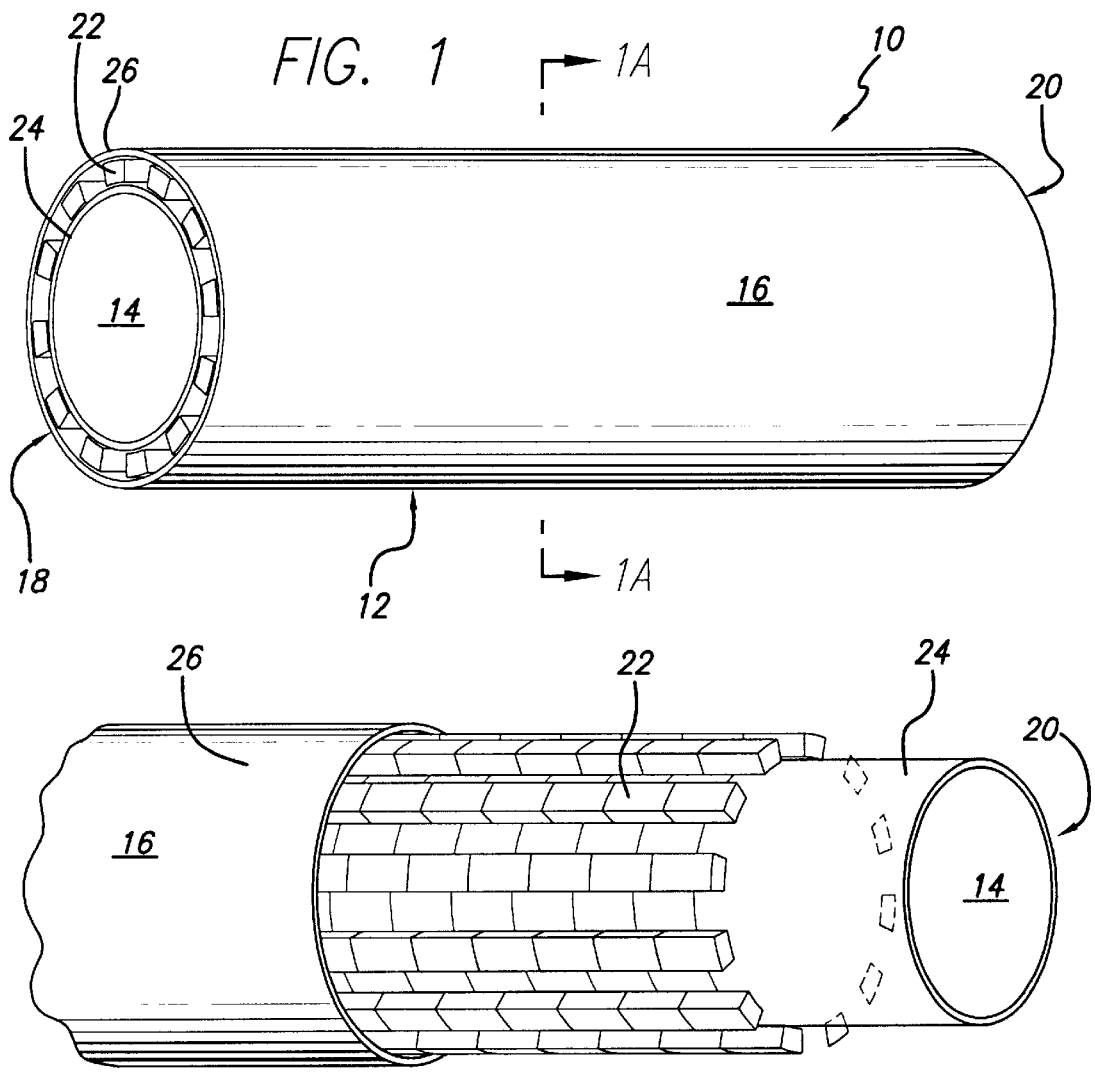
FIG. 1
FIG. 2
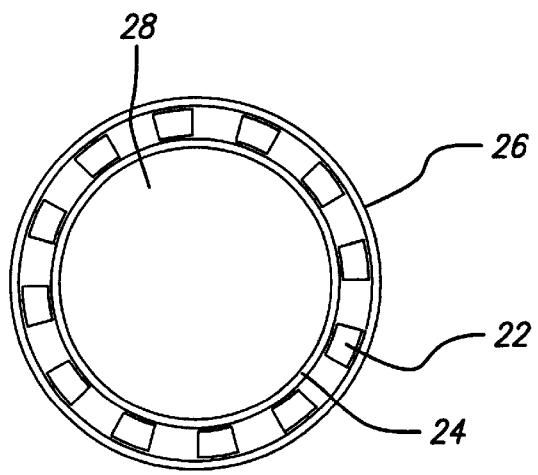
FIG. 1A

ENCAPSULATED STENT

This application is a continuation of U.S. application Ser. No. 08/401,871, filed Mar. 10,1995, now U.S. Pat. No. 6,124,523.

BACKGROUND OF THE INVENTION

1. Field of the Invention

The present invention relates generally to an encapsulated stent comprising a stent inseparably contained between two grafts wherein the, grafts are preferably comprised of expanded polytetrafluoroethylene (ePTFE) and, in addition, to a method for making an encapsulated stent. More particularly, one preferred embodiment of the present invention relates to a radially expandable encapsulated stent for implantation within the vascular system which comprises a balloon expandable tubular stent member which is sandwiched between two tubular shaped ePTFE members. The tubular shaped members may also be comprised of unexpanded polytetrafluoroethylene (ePTFE). The method for making the encapsulated stent includes concentrically positioning the stent between the graft members, applying pressure to the assembly to fuse the graft layers to one another through the openings between the struts of the stent, and sintering the assembly.

2. Description of Related Art

The use of implantable vascular grafts comprised of PTFE are well known in the art. These types of grafts are typically used to replace or repair damaged or occluded blood vessels within the body. However, once such grafts are radially expanded within a blood vessel, they exhibit some retraction subsequent to expansion. Further, they require additional means for anchoring the graft within the blood vessel, such as sutures, clamps, or similarly functioning elements. In order to overcome the retraction disadvantage and eliminate the additional attachment means, those skilled in the art have used stents such as those presented by Palmaz in U.S. Pat. No. 4,733,665 and Gianturco in U.S. Pat. No. 4,580,568, which are herein incorporated by reference, either alone or in combination with PTFE grafts, in order to provide a non-retracting prosthesis having self-anchoring capability.

For example, the stent described by Palmaz in U.S. Pat. No. 4,733,665 is used to repair an occluded blood vessel by introducing the stent into the blood vessel via a balloon catheter, positioning the stent at the occluded site contained within the blood vessel, and expanding the stent to a diameter which is comparable to the diameter of the unoccluded blood vessel. The balloon catheter is then removed and the stent remains seated within the blood vessel due to the stent's ability to undergo radial expansion while limiting radial retraction. Further, use of radially expandable stents in combination with a PTFE graft is disclosed in U.S. Pat. No. 5,078,726 to Kreamer. Kreamer teaches placing a pair of expandable stents within the interior ends of a prosthetic graft having a length which is sufficient to span the weakened section of a blood vessel. The stents are then expanded to an increased diameter thereby securing the graft to the blood vessel wall via a friction fit.

However, although stents and stent/graft combinations have been used to provide endovascular prostheses which are capable of maintaining their fit against blood vessel walls, other desirable features are lacking. For instance, features such as increased strength and durability of the prosthesis, as well as an inert, smooth, biocompatible blood flow surface on the luminal surface of the prosthesis and an inert, smooth biocompatible surface on the abluminal surface of the prosthesis, are considered to be advantageous characteristics for an implantable vascular graft. Some of those skilled in the art have recently addressed these desirable characteristics by producing strengthened and reinforced prostheses composed entirely of biocompatible grafts and graft layers.

For example, U.S. Pat. No. 5,048,065, issued to Weldon et al. discloses a reinforced graft assembly comprising a biologic or biosynthetic graft component having a porous surface and a biologic or biosynthetic reinforcing sleeve which is concentrically fitted over the graft component. The reinforcing sleeve includes an internal layer, an intermediate layer, and an external layer, all of which comprise biocompatible fibers. The sleeve component functions to provide compliant reinforcement to the graft component. Further, U.S. Pat. No. 5,163,951, issued to Pinchuk et al. describes a composite vascular graft having an inner component, an intermediate component, and an outer component. The inner and outer components are preferably formed of expanded PTFE while the intermediate component is formed of strands of biocompatible synthetic material having a melting point less than the material which comprises the inner and outer components.

Another reinforced vascular prosthesis having enhanced compatibility and compliance is disclosed in U.S. Pat. No. 5,354,329, issued to Whalen. The Whalen patent describes a non-pyrogenic vascular prosthesis comprising a multilaminar tubular member having an interior strata, a unitary medial strata, and an exterior strata. The medial strata forms an exclusionary boundary between the interior and exterior strata. Also, one embodiment of the prosthesis is formed entirely of silicone rubber which comprises different characteristics for the different strata contained within the graft.

The prior art also includes grafts having increased strength and durability which have been reinforced with stent-like members. For example, U.S. Pat. No. 4,731,073, issued to Robinson discloses an arterial graft prosthesis comprising a multi-layer graft having a helical reinforcement embedded within the wall of the graft. U.S. Pat. No. 4,969,896, issued to Shors describes an inner elastomeric biocompatible tube having a plurality of rib members spaced about the exterior surface of the inner tube, and a perforate flexible biocompatible wrap circumferentially disposed about, and attached to, the rib members.

Another example of a graft having reinforcing stent-like members is disclosed in U.S. Pat. No. 5,123,917, issued to Lee. The Lee patent describes an expandable intraluminal vascular graft having an inner flexible cylindrical tube, an outer flexible cylindrical tube concentrically enclosing the inner tube, and a plurality of separate scaffold members positioned between the inner and outer tubes. Further, U.S. Pat. No. 5,282,860, issued to Matsun, et al. discloses a multi-layer stent comprising an outer resin tube having at least one flap to provide an anchoring means, an inner fluorine based resin tube and a mechanical reinforcing layer positioned between the inner and outer tubes.

Another stent containing graft is described in U.S. Pat. No. 5,389,106, issued to Tower. The Tower patent discloses an impermeable expandable intravascular stent which includes a distensible frame and an impermeable deformable membrane interconnecting portions of the frame to form an impermeable exterior wall. The membrane comprises a synthetic non-latex, non-vinyl polymer while the frame is comprised of a fine platinum wire. The membrane is attached to the frame by placing the frame on a mandrel, dipping the frame and the mandrel into a polymer and organic solvent solution, withdrawing the frame and mandrel from the solution, drying the frame and mandrel, and removing the mandrel from the frame.

Although the previously described reinforced grafts disclose structures which have increased strength and durability, as well as inert, smooth inner and outer surfaces to reduce thrombogenicity, the prior art references do not disclose a device which exhibits these advantageous characteristics in addition to good resistance to radial contraction and possible self anchoring means. Accordingly, there is a need for a radially expandable reinforced vascular graft having good resistance to radial contraction and means for self anchoring which also exhibits increased strength, increased durability, and inertness with respect to its interior and exterior surfaces.

SUMMARY OF THE INVENTION

It is a principal object of the present invention to provide a reinforced vascular graft in the form of an encapsulated stent having self-anchoring means, increased strength and increased resistance to radial retraction.

It is a further object of the present invention to provide a reinforced vascular graft in the form of an encapsulated stent having inert, smooth, biocompatible interior and exterior surfaces to reduce thrombogenicity associated with the surfaces of the graft.

It is still a further object of the present invention to provide a radially expandable reinforced vascular graft in the form of an encapsulated stent that can be used with any conventional balloon catheter and which easily detaches from the balloon catheter upon deflation of the balloon without exhibiting recoil of the graft onto the balloon.

It is yet a further object of the present invention to provide a one-piece radially expandable reinforced vascular graft which comprises a stent or similarly structured support layer and dual PTFE graft layers which are inseparable both in vivo and in vitro.

It is a still further object of the present invention to provide an encapsulated stent comprising a stent member sandwiched between two PTFE graft members.

It is yet another object of the present invention to provide an encapsulated stent comprising a tubular stent circumferentially sandwiched between two tubular PTFE grafts wherein the length of the PTFE grafts are less than or equal to the length of the stent at an expanded diameter.

It is still another object of the present invention to provide an encapsulated stent comprising at least two tubular stents circumferentially sandwiched between the ends of two tubular shaped PTFE grafts wherein the length of the PTFE grafts is greater than the length of the stents and a region of the PTFE grafts is unsupported by the stents. Further, the encapsulated stent may take the form of an articulated configuration in which there are a series of unsupported PTFE graft areas disposed between stent supported PTFE graft areas.

It is another object of the present invention to provide a method for making an encapsulated stent which comprises inseparable layers of PTFE graft, stent, and PTFE graft.

Briefly, the present invention generally comprises a radially expandable reinforced vascular graft which includes a first layer of biocompatible flexible material, a second layer of biocompatible flexible material, and a support layer sandwiched between the first and second layers of biocompatible flexible material. The biocompatible flexible layers are preferably comprised of expanded PTFE, but may comprise unexpanded PTFE. The support layer preferably comprises a stent and may be made of any strong material which can undergo radial expansion but resists radial collapse such as silver, titanium, stainless steel, gold, or any suitable plastic material capable of maintaining its shape and material properties at sintering temperatures and having the necessary strength and elasticity to enable uniform expansion without collapse. A preferred embodiment of the radially expandable reinforced vascular comprises a tubular stent cover having a first biocompatible flexible tubular member, a tubular shaped support member concentrically positioned about the outer surface of the first biocompatible flexible tubular member, and a second biocompatible flexible tubular member concentrically positioned about the outer surface of the tubular shaped support member wherein the tubular members form inseparable layers. The tubular shaped support member preferably comprises a plurality of openings to enable the first and second biocompatible flexible tubular members to be fused together through the openings thereby forming flexible tubular member circumferentially positioned about the outer surface of the first biocompatible flexible tubular member, and at least one tubular support member sandwiched between an end portion of the first and second biocompatible flexible tubular members such that the inner surface of the support member is adjacent to the outer surface of the first biocompatible member and the outer surface of the support member is adjacent the inner surface of the second biocompatible member thereby encapsulating the stent. A second tubular support member may be concentrically sandwiched between the opposite ends of the first and second biocompatible flexible tubular members to form a stented graft having ends comprising stents or support members encapsulated in ePTFE and a middle ePTFE graft portion that is unsupported by stents. Additional and/or other types of structural supports may also be encapsulated between inner and outer flexible biocompatible members as described above to form varying embodiments of the reinforced vascular graft. For example, an expandable, articulated reinforced vascular graft may be formed by sandwiching a structural support assembly comprising multiple stent members spaced apart from one another between two biocompatible tubular members. The resulting expandable, articulated reinforced vascular graft is a monolithic structure which is incapable of separation or delamination. The structural support assembly appears to be embedded within the wall of the expandable, articulated reinforced vascular graft.

The biocompatible material used in all of the above-described embodiments may comprise polytetrafluoroethylene, polyamides, polyimides, silicones, fluoroethylpolypropylene (FEP), polypropylfluorinated amines (PFA), or any other fluorinated polymers.

The present invention is also directed to a process for making a radially expandable reinforced vascular graft which includes the steps of:
a) positioning a layer of pressure expandable support material having a plurality of openings over a first layer of flexible biocompatible graft material having a top and bottom surface;
b) positioning a second layer of flexible biocompatible graft material having a top surface and a bottom surface over said layer of support material such that said layer of support material is sandwiched between said first and second layers of flexible biocompatible graft material; and
c) fixing said layer of support material to said first and second layers of flexible biocompatible graft material such that all of said layers are inseparable.

The step of fixing the support layer to the biocompatible graft layers may comprise applying pressure to the layers after they are loaded onto a mandrel and then heating the resulting assembly at sintering temperatures to form a mechanical bond, or applying at least one of an adhesive, an aqueous dispersion of polytetrafluoroethylene, a polytetrafluoroethylene tape, fluoroethylpolypropylene (FEP), or tetrafluoroethylene between the flexible biocompatible graft layers and the support layer and heating the resulting assembly at a melt temperature below the sintering temperature of the biocompatible graft layers.

Further, the process for making a preferred embodiment of the radially expandable reinforced vascular graft of the present invention includes the steps of:

a) placing a first expanded unsintered tubular shaped polytetrafluoroethylene graft onto a mandrel;

b) placing a tubular shaped support structure having a plurality of openings over said first graft;

c) placing a second expanded unsintered tubular shaped polytetrafluoroethylene graft having a larger diameter than said first graft over said tubular shaped support structure; and d) fixing said first and second tubular graft members to said tubular support structure such that all of said members are inseparable.

As in the general process for making an expandable reinforced vascular graft, the step of fixing the first and second tubular graft members to the tubular support structure may comprise applying pressure to the tubular members after they are loaded onto a mandrel followed by heating the resulting assembly to sintering temperatures for the ePTFE tubular members in order to form a mechanical bond. Alternatively, the fixing process may include the step of applying at least one of an adhesive, an aqueous dispersion of polytetrafluoroethylene, a polytetrafluoroethylene tape, FEP, or tetrafluoroethylene between the tubular ePTFE grafts and the tubular support structure and heating the resulting assembly at a melt temperature below the sintering temperature of the tubular ePTFE grafts.

These and other objects, features and advantages of the present invention will become more apparent to those skilled in the art when taken with reference to the following more detailed description of the preferred embodiments of the invention in conjunction with the accompanying drawings.

BRIEF DESCRIPTION OF THE DRAWINGS

FIG. 1 is a perspective view of a first preferred embodiment of the encapsulated stent of the present invention comprising a tubular shaped stent cover configuration in an unexpanded condition.

FIG. 1A is a cross-sectional view of the tubular shaped stent cover shown in FIG. 1 taken along line 1A—1A of FIG. 1.

FIG. 2 is a partially exploded view of the first preferred embodiment of the encapsulated stent of the present invention shown in FIG. 1.

DETAILED DESCRIPTION OF THE PREFERRED EMBODIMENT

Figure 3:
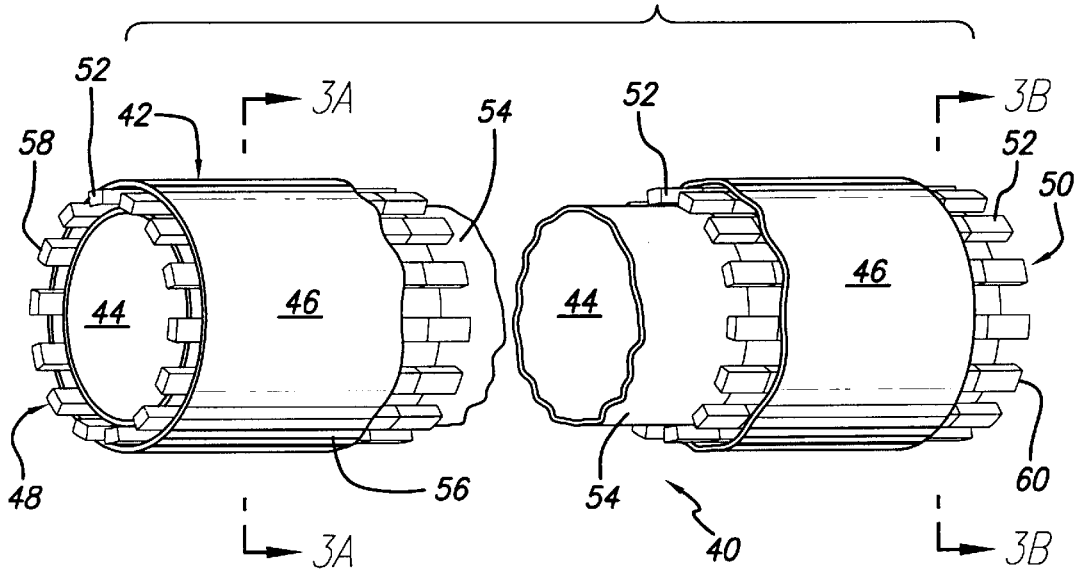
FIG. 3 is a perspective view of a second preferred embodiment of the tubular shaped stent cover configuration of the present invention wherein the lengths of the grafts are less than the length of the stent with parts shown cut away to expose the underlying layers.

Referring now to the figures, where the reference numerals represent various elements of the present invention, a first preferred embodiment of the encapsulated stent which comprises a tubular stent cover 10 is shown in FIG. 1. The tubular stent cover 10 generally comprises a tubular member 12 having an interior surface 14 and an exterior surface 16 which are contained between first and second ends 18, 20. As illustrated in FIGS. 1 and 2, the tubular member 12 comprises a balloon or pressure expandable tubular shaped support member 22 which is loaded over a first biocompatible flexible tubular member 24 which is held on a mandrel (not shown). A second biocompatible flexible tubular member 26 is then loaded over the first biocompatible tubular member/support member combination. The tubular shaped support member 22 preferably comprises a stent like that described in U.S. Pat. No. 4,733,665, issued to Palmaz, and which is herein incorporated by reference, and the first and second biocompatible flexible tubular members 24, 26 are preferably comprised of expanded polytetrafluoroethylene (ePTFE). The first and second biocompatible flexible tubular members 24, 26 may also be comprised of unexpanded polytetrafluoroethylene (PTFE). Further, the pressure expandable tubular shaped support member 22 may be comprised of any material having the strength and elasticity to permit radial expansion and resist radial collapse such as silver, titanium, stainless steel, gold, and any suitable plastic material capable of maintaining its shape and material properties at sintering temperatures.

A cross sectional view of the tubular stent cover 10 shown in FIG. 1, taken along line 1A—1A, prior to fusing the graft members and prior to expansion, is shown in FIG. 1A. The first biocompatible flexible tubular member 24, preferably comprised of unsintered ePTFE, forms the innermost layer or luminal surface of the tubular stent cover 10, and covers the lumen 28 of the tubular stent cover 10, thereby providing a smooth, inert biocompatible blood flow surface. The tubular support member 22, preferably comprising a Palmaz stent or similarly constructed structure, forms the middle layer located at the center of the tubular stent cover 10. Finally, the second biocompatible flexible tubular member 26, which is also preferably comprised of unsintered ePTFE, forms the outermost layer or abluminal surface of the tubular stent cover 10.

After loading the tubular shaped members onto one another, pressure is applied to the graft/stent/graft assembly in order to fuse the first and second biocompatible flexible tubular members 24, 26 to one another through the openings contained within the tubular support member 22. Where the tubular support member 22 comprises a stent, the first and second ePTFE tubular members 24, 26 are fused to one another through the openings between the struts of the stent. The graft/stent/graft assembly is then heated at sintering temperatures to form a mechanical bond between the ePTFE layers. The resulting prosthesis is an unexpanded stent encapsulated within ePTFE layers, or more accurately, an unexpanded stent having ePTFE layers on its luminal and abluminal surfaces, respectfully, wherein the stent and ePTFE layers are inseparable. However, the ePTFE layers may also be fused or joined together around the ends of the unexpanded stent thereby entirely encasing the stent within ePTFE in both the radial and longitudinal directions.

Figure 5:
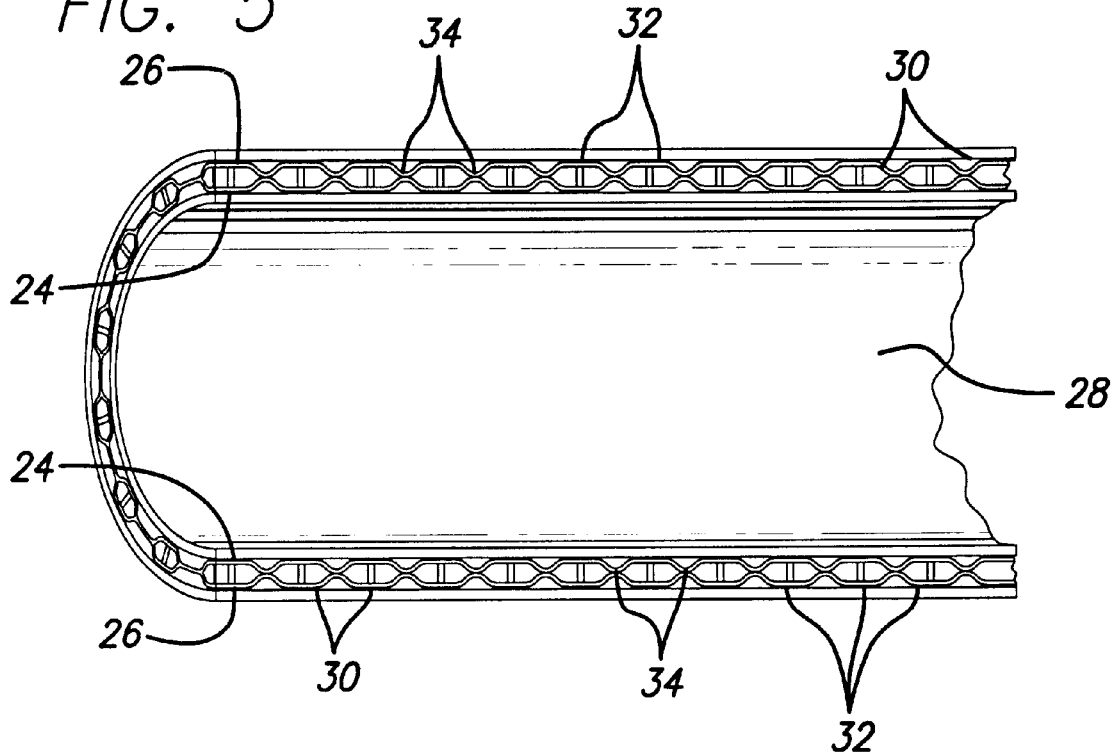
FIG. 5 is a partial longitudinal cross-sectional view of the tubular shaped stent cover shown in FIG. 1 after fusing the tubular graft members together through the struts of the stent.
Figure 6:
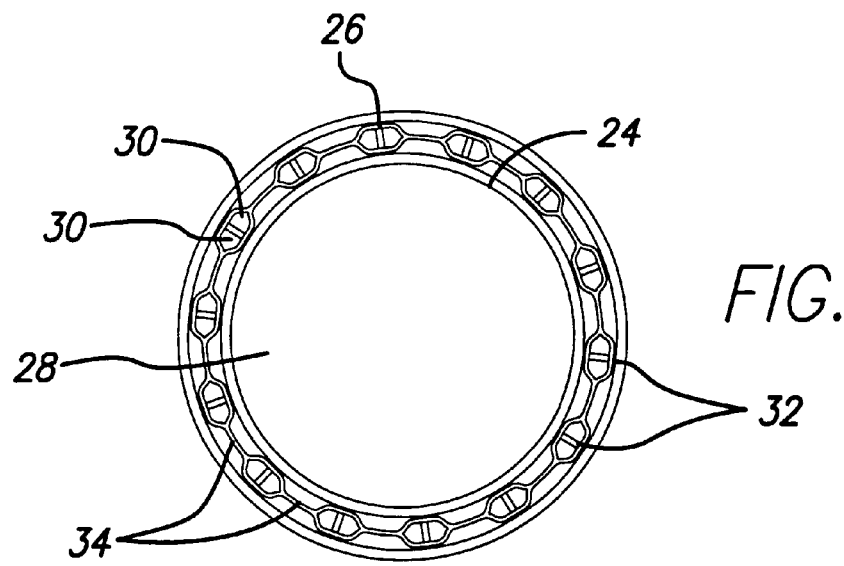
FIG. 6 is a vertical cross-sectional view of the tubular shaped stent cover shown in FIG. 1 after fusing the tubular graft members together through the struts of the stent.

FIG. 5 shows a partial longitudinal cross-sectional view of the tubular shaped stent cover 10 shown in FIG. 1 after fusing the tubular graft members 24, 26 together through the struts of the stent. The tubular support member 22, i.e. the stent, comprises openings 30 between struts 32. The first and second biocompatible flexible tubular members 24, 26 are fused together between the openings 30 to form sealed areas 34 between struts 32. FIG. 6 depicts a vertical cross-sectional view of the tubular shaped stent cover 10 shown in FIG. 1 after fusing the tubular graft members 24, 26 together through the struts 32 of the stent 22. As seen in FIG. 6, the first biocompatible flexible tubular member 24 forms the inner layer which covers the lumen 28 thereby forming the luminal surface of the tubular stent cover 10 and the second biocompatible flexible tubular layer 26 forms the outermost layer and abluminal surface of the tubular stent cover 10. The tubular support structure 22, or stent, forms the middle layer of the prosthesis. The first and second biocompatible flexible tubular layers 24, 26 fuse together through the openings 30 located between the struts 32 of the stent 22 to form sealed areas 34. In order to promote clarity, FIGS. 5 and 6 illustrate an exaggeration of the remaining open areas surrounding the struts 32 of the stent. Further, upon expansion of the tubular stent cover 10, the struts 32 of the stent appear to be buried within the walls of the first and second biocompatible flexible tubular members 24, 26 and no open areas remain between the biocompatible tubular members 24, 26.

Subsequent to applying pressure to the graft/stent/graft assembly and sintering the same to mechanically bond the ePTFE, the assembly is removed from the mandrel and is ready for implantation into the endovascular system. The graft/stent/graft assembly which comprises the tubular stent cover 10 is then loaded onto a balloon catheter and introduced and positioned within a targeted blood vessel or other luminal body regions.

All tubular embodiments of the radially expandable reinforced vascular graft are designed to be used with conventional balloon catheters making the delivery system for the device simple, easily accessible, and cost effective. Once in the tubular stent cover 10 is properly positioned, the tubular stent cover 10 is expanded using the balloon catheter. During expansion, the ePTFE between the stent struts 32 expands radially to accommodate the stent 22 expansion. No layer separation occurs. The tubular stent cover 10 does not delaminate. After radial expansion, the tubular stent cover 10 appears as a tubular ePTFE graft having a tubular support structure 22, or stent, imbedded within its walls. The ePTFE present in the radially expanded tubular stent cover 10 exhibits all the physical characteristics of the tubular stent cover's 10 base-sintered graft. Further, additional features may be added, such as barbs at the ends 18, 20 of the tubular member 12 which comprises the tubular stent cover 10, in order to facilitate anchoring of the device within a blood vessel wall.

Turning now back to FIG. 3, there is shown a second preferred embodiment of the tubular shaped stent cover configuration of the present invention wherein the lengths of the grafts are less than the length of the stent. FIG. 3 depicts a perspective view of the second embodiment of the present invention comprising the alternative tubular stent cover 40 shown partially cut away to expose the underlying members which comprise part of the tubular stent cover 40. The alternative tubular stent cover 40 comprises a tubular member 42 having an interior surface 44, an exterior surface 46, and first and second ends 48, 50. The tubular member 42 includes a pressure expandable tubular support member 52, which preferably comprises a Palmaz stent incorporated herein by reference to exemplify a type of endovascular stent for use with the invention, that is sandwiched between first and second biocompatible tubular members 54, 56, which are preferably comprised of ePTFE, all of which are capable of being radially expanded. The tubular support member 52 is greater in length than the first and second biocompatible tubular members 54, 56. This, allows the first and second ends 58, 60 of the tubular support member 52 to form barbs upon expansion of the tubular stent cover 40 which radially project outwardly from the longitudinal axis of the stent, and help to anchor the alternative tubular stent cover 40 to the targeted blood vessel wall. Further, the ends of the tubular stent cover 40 may form funnel shaped ends. These funnel shaped ends function to channel the blood flow into the stent and act as an internal guide to facilitate subsequent catheterization of the stented vessel, minimize embolism formation between surfaces external to the stent and the stent wall, and further facilitate the placement and anchoring of the encapsulated stent.

As previously mentioned, the tubular support member 52 preferably comprises a pressure expandable stent and the first and second biocompatible flexible tubular members 54, 56 are preferably comprised of unsintered ePTFE at the beginning of the process for making the encapsulated stent. However, additional embodiments and methods for making the encapsulated stent are contemplated. These additional embodiments and methods include sandwiching a stent between extruded, but unexpanded and unsintered PTFE tubular grafts, and attaching the layers of ePTFE to both surfaces or sides of a stent by means other than applying pressure and sintering, such as applying an adhesive, an aqueous dispersion of PTFE, a PTFE tape, FEP, or a tetrafluoroethylene between the layers of graft and the stent and then heating the assembly to melting temperature below the sintering temperature of the graft layers.

The second biocompatible tubular member 56 is cut away to reveal the underlying tubular support member 52, which is further cut away to reveal the first biocompatible tubular member 54. The first and second biocompatible tubular members 54, 56 may be of the same length as shown in FIG. 1. The first and second biocompatible tubular members 54, 56 may also be shorter in length than the tubular support member 52. This permits the first and second ends 58, 60 of the tubular support layer 52 to flare radially outward beyond the first and second ends of the first and second biocompatible tubular members 54,.56 during radial expansion of the stent cover 40. This flaring of the tubular support members, or stent's, ends facilitates the anchoring of the encapsulated stent into the wall of a blood vessel. Further, the lengths of the biocompatible tubular members 54, .56 may be adjusted to provide flared or funnel shaped ends that are covered by biocompatible graft material such as ePTFE.

Figure 3A:
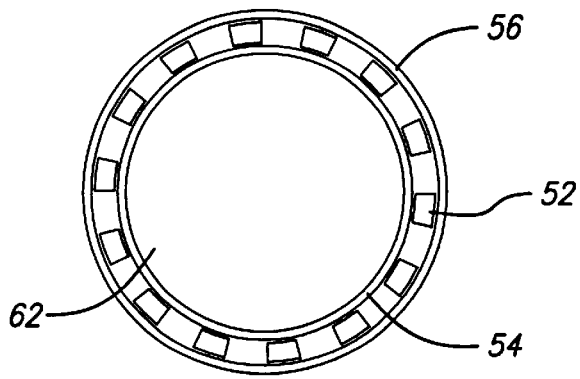
FIG. 3A is a cross-sectional view of the tubular shaped stent cover shown in FIG. 3 taken along line 3A—3A of FIG. 3.

A cross-sectional view taken along line 3A—3A near the center of the alternative tubular stent cover 40 of the present invention illustrated in FIG. 3 is shown in FIG. 3A. The first biocompatible tubular layer 54, preferably comprised of expanded unsintered PTFE, forms the innermost layer and luminal surface of the alternative tubular stent cover 40 and covers the lumen 62 of the alternative tubular stent cover 40. The tubular support member 52, preferably comprising a Palmaz stent herein incorporated by reference to exemplify a type of endovascular stent for use with the invention, or similarly constructed structure, forms the middle layer of the alternative tubular stent cover 40. Finally, the second biocompatible tubular member 56, which also preferably comprises expanded unsintered PTFE, forms the outermost layer and abluminal surface of the alternative tubular stent cover 40.

Figure 3B:
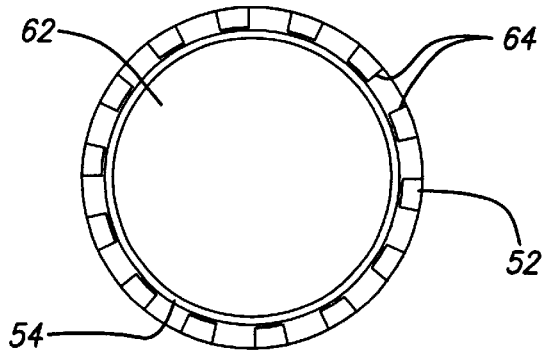
FIG. 3B is a cross-sectional view of the tubular shaped stent cover shown in FIG. 3 taken along line 3B—3B of FIG. 3.

FIG. 3B illustrates a cross-sectional view of the alternative tubular stent cover 40 shown in FIG. 3 taken along line 3B—3B near the second end 50 of the tubular member 42 which comprises the alternative tubular stent cover 40. The innermost layer, or luminal surface, is formed by the first biocompatible tubular member 54 which covers the lumen 62 of the stent cover 40. The next and outermost layer is formed by the tubular support member 52, or stent, which covers the first biocompatible tubular member 54 and forms the abluminal surface of the stent cover 40. As previously described, the tubular support member 52 comprises a Palmaz stent having struts 64, or a similarly constructed structure, but may be comprised of any material capable of retaining its shape and material properties under sintering temperatures and having the strength and elasticity to permit radial expansion and resist radial collapse.

Figure 4:
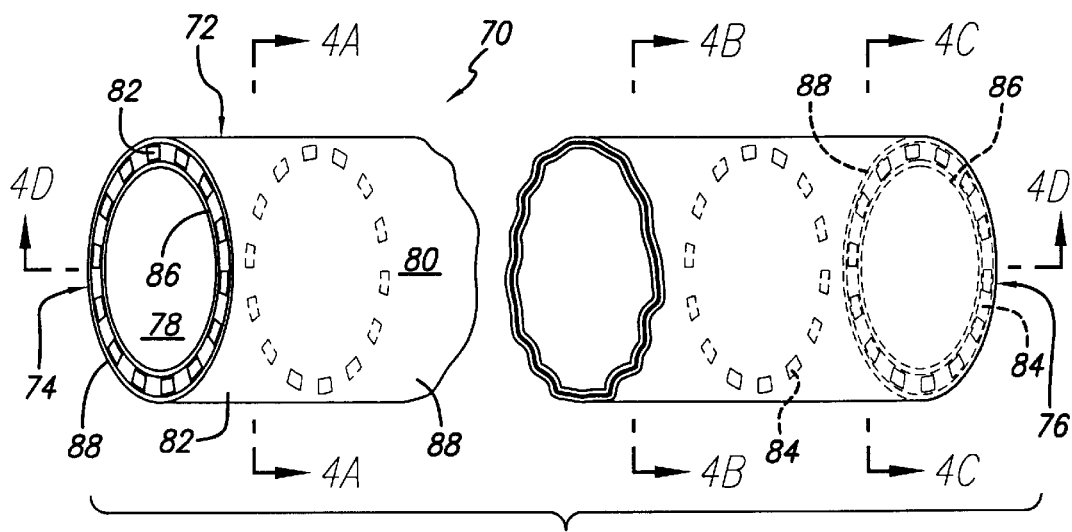
FIG. 4 is a perspective view of a third preferred embodiment of the encapsulated stent of the present invention comprising a tubular shaped stented graft having two stents, shown in phantom, sandwiched between two grafts wherein a region of the overlapping grafts are unsupported by the stents.

A third preferred embodiment of the encapsulated stent of the present invention is illustrated in FIG. 4 and FIGS. 4A–4D. As shown in FIG. 4, the third preferred embodiment comprises a tubular shaped stented graft 70 comprising a tubular member 72 having a first end 74, a second end 76, an interior surface 78, and an exterior surface 80. The tubular member 72 includes first and second pressure expandable tubular support members 82, 84, preferably comprising Palmaz stents, shown in phantom, that are sandwiched between the ends of first and second biocompatible tubular members 86, 88, respectively, wherein there is a longitudinal region of overlapping first and second biocompatible tubular members 86, 88, which is unsupported by the stents 82, 84. The first and second tubular support members 82, 84 may comprise structured configurations similar to stents and may be comprised of a suitable material having sufficient strength and elasticity to permit radial expansion and resist radial collapse. Further, the first and second biocompatible tubular members 86, 88 are preferably comprised of unsintered ePTFE, but may also be comprised of unsintered PTFE.

Figures 4A, 4B, 4C:
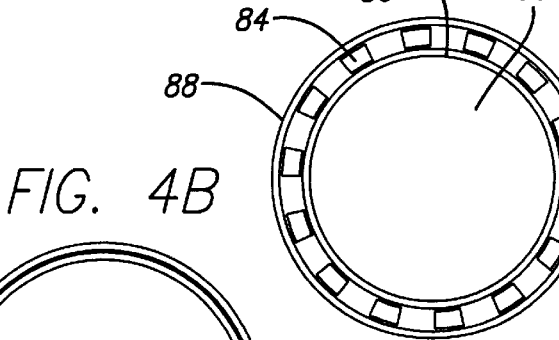
FIG. 4A is a cross-sectional view of the tubular shaped stented graft shown in FIG. 4 taken along line 4A—4A of FIG. 4.
FIG. 4B is a cross-sectional view of the tubular shaped stented graft shown in FIG. 4 taken along line 4B—4B of FIG. 4.
FIG. 4C is a cross-sectional view of the tubular shaped stented graft shown in FIG. 4 taken along line 4C—4C of FIG. 4.

As shown in the vertical cross-sectional views depicted in FIGS. 4A and 4C which are taken along line 4A—4A and line 4D—4D of FIG. 4, respectively, the end portions of the tubular shaped stented graft embodiment 70 comprise an innermost layer formed by the first biocompatible tubular member 86 which covers the lumen 90 of the graft and forms the luminal surface of the stented graft 70. FIGS. 4A–4D represent the tubular shaped stented graft 70 prior to applying pressure to the graft to fuse the biocompatible members 86, 88 and prior to sintering. The middle layer at each of the ends of the tubular shaped stented graft 70 is formed by the first and second tubular support members 82, 84, respectively. Finally, the second biocompatible tubular member 88 forms the outermost layer and abluminal surface of the stented graft 70 located near the first and second ends 74, 76 of the tubular member 72 which comprises the stented graft 70.

FIG. 4B shows a vertical cross-sectional view near the center of the stented graft 70 shown in FIG. 4 taken along line 4B—4B of FIG. 4. The center portion of the stented graft 70 shown in FIG. 4 is unsupported by any type of stent or tubular support member and simply comprises a lumen 90, which is surrounded by an innermost ePTFE graft layer formed from the first biocompatible tubular member 86, and an outermost ePTFE graft layer concentrically retained around the outer surface of the first biocompatible tubular member 86 and formed from the second biocompatible tubular member 88. Subsequent to applying pressure to the double stented graft/stent/graft assembly, and subsequent to sintering the assembly, the first and second biocompatible tubular members 86, 88 form inseparable layers along their entire length.

Figure 4D:
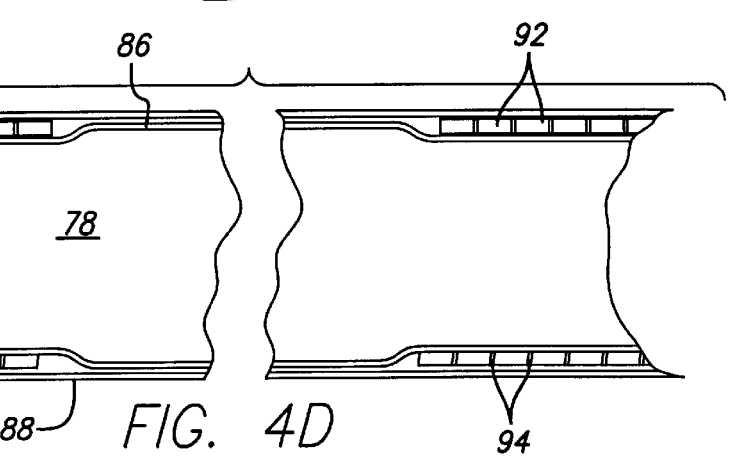
FIG. 4D is a longitudinal cross-section of the tubular shaped stented graft shown in FIG. 4 taken along line 4D—4D of FIG. 4.

A partial longitudinal cross-sectional view of the stented graft 70 shown in FIG. 4 taken along line 4D—4D of FIG. 4 is illustrated in FIG. 4D. Like FIGS. 4A–4C, this visual representation of the stented graft 70 represents the stented graft 70 prior to fusing the first and second biocompatible tubular members 86, 88 together through the openings 92 contained between the struts 94 of the first and second tubular support members 82, 84. The first and second tubular support members 82, 84 are sandwiched between the first and second biocompatible tubular members 86, 88. At this processing stage, all of the tubular members 82, 84, 86, 88 have not yet formed inseparable layers.

Figure 7:
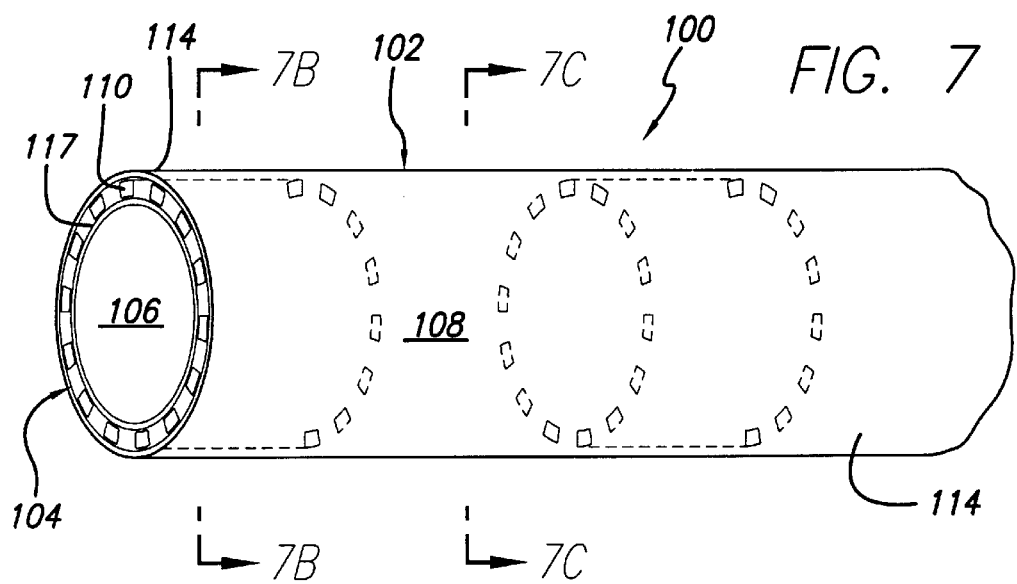
FIG. 7 is a perspective view of a fourth preferred embodiment of the encapsulated stent of the present invention comprising an articulated stented graft having a plurality of stents, shown in phantom, sandwiched between two tubular shaped grafts.
Figure 7A:
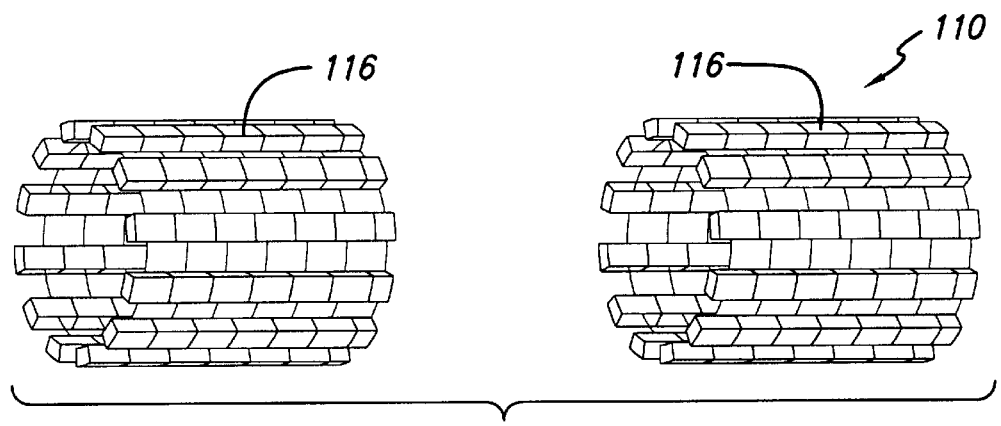
FIG. 7A is the support structure contained within the graft shown in FIG. 7 comprising a plurality of stents.

FIG. 7 illustrates a fourth preferred embodiment of the encapsulated stent of the present invention comprising an articulating stented graft 100 generally comprising a tubular member 102 having a first end 104, a second end (not shown), an interior surface 106, and an exterior surface 108. The tubular member 102 includes a plurality of stent members 116 sandwiched between first and second tubular shaped biocompatible grafts 112, 114. A perspective view of the plurality of stent members is shown in FIG. 7A. The plurality of stent members 116 are spaced apart from one another at a predetermined distance. The spaced apart stent members 116 allow the encapsulated stent 100 to articulate between stent members 116.

Figures 7B, 7C:
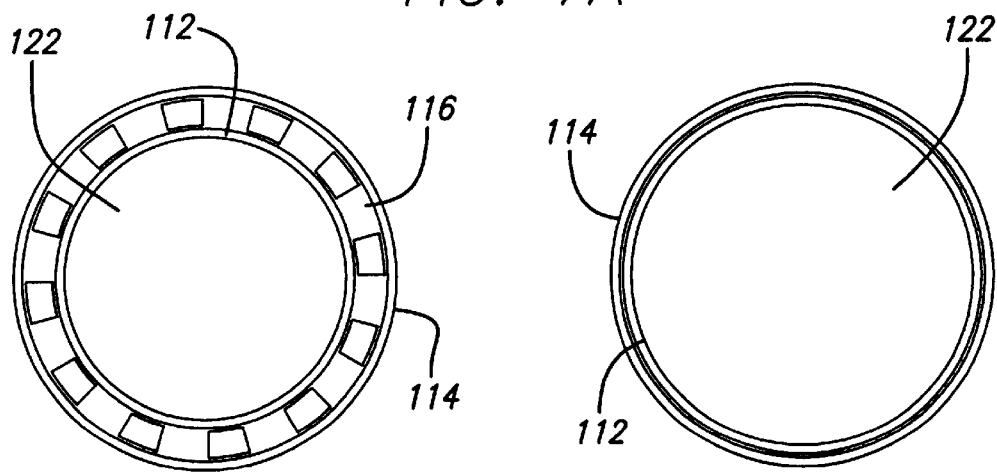
FIG. 7B is a cross-sectional view of the articulated stented graft shown in FIG. 7 taken along line 7B—7B of FIG. 7.
FIG. 7C is a cross-sectional view of the articulated stented graft shown in FIG. 7 taken along line 7C—7C of FIG. 7.

FIG. 7B shows a cross-sectional view near the end of the articulating encapsulated stent 100 illustrated in FIG. 7 taken 25 along line 7B—7B of FIG. 7. The first tubular shaped biocompatible graft 112 forms the innermost layer which surrounds the lumen 122 of the articulating stented graft 100. The middle layer is formed by a stent member 116 contained between the first and second tubular shaped biocompatible grafts 112, 114, and the outermost layer is formed from the second tubular shaped biocompatible graft 114.

FIG. 7C shows a cross-sectional view near a substantially unsupported middle section of the articulating stented graft 100 illustrated in FIG. 7 taken along line 7C—7C of FIG. 7. The first tubular shaped biocompatible graft 112 forms the inner layer while the second tubular shaped biocompatible graft 114 forms the outer layer.

All of the previously described compositions for both of the biocompatible flexible members included in the stent cover, the stented graft, and the articulating stented graft, are preferably expandable.

Figure 8:
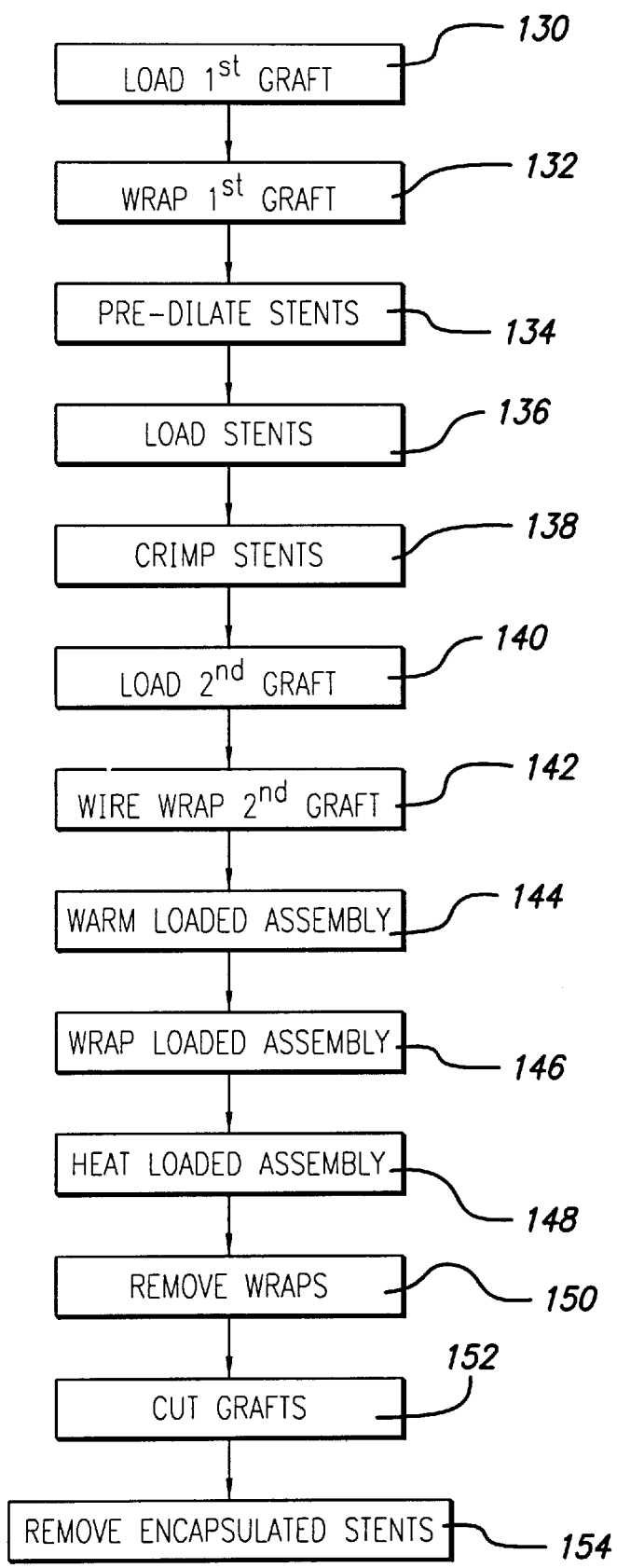
FIG. 8 is a flowchart of the process for making the first preferred embodiment of the encapsulated stent of the present invention.

FIG. 8 illustrates a flow chart which depicts the process for making the preferred embodiment of the radially expanded encapsulated stent. The first, step one 130 involves loading a first ePTFE graft onto a mandrel. A section of the first ePTFE graft is then wrapped with wire or tape to prevent migration of the first ePTFE graft on the mandrel in step two 132. The next step, step three 134, comprises pre-dilating one or more stents on a second mandrel. Once the stents are pre-dilated, the stents are loaded over the first ePTFE graft and mandrel and spaced apart evenly along the length of the first ePTFE graft in step four 136. In step five 138, the pre-dilated stents are crimped onto the first graft and mandrel. Subsequent to crimping the pre-dilated stents, a second ePTFE graft is loaded over the crimped stents in step six 140. The next step, step seven 142, requires wrapping the second ePTFE graft at its ends and between the crimped stents with a wire wrap. Next, the assembly comprising the mandrel, the first ePTFE graft, the crimped stents, and the second ePTFE graft is warmed in an oven in step eight 144. After warming, the entire assembly is wrapped with TEFLON tape as indicated in step nine 146. In step ten 148, the wrapped assembly is then heated to sintering temperatures. After heating at sintering temperatures, the assembly is removed from the oven, and the tape and wire wraps are removed from the assembly in step eleven 150. Step twelve 152 involves carefully cutting the ePTFE grafts near the ends of the stents to form individual encapsulated stents. Finally, in step thirteen 154, the resulting encapsulated stents are removed from the mandrel.

The following examples describe the preparation of the preferred embodiment of the invention which comprises the tubular shaped encapsulated stent. The examples are meant to be purely illustrative and nonlimiting.

Example 1

A three millimeter (mm) internal diameter (ID) thin wall ePTFE vascular graft was loaded onto a 3.56 mm mandrel. The top section of the ePTFE graft was wrapped with TEFLON tape to prevent slippage on the mandrel. Next, two P-394 "PALMAZ" stents and two P-308 "PALMAZ" stents were pre-dilated on a 4.74 mm mandrel. The pre-dilated stents were then loaded over the 3 mm ePTFE graft and spaced equidistantly from one another along the length of the 3 mm ePTFE graft. The pre-dilated stents were then crimped down onto the mandrel and the outer surface of the 3 mm ePTFE graft. Next, a 4 mm ID graft was loaded over the crimped stents. The 4 mm ePTFE graft was wire wrapped onto the assembly at its ends and between the crimped stents. Subsequent to the loading steps, the wrapped assembly was then warmed in an oven at 340° C. for thirty seconds and then removed. The entire assembly was then tightly wrapped with TEFLON tape and placed back into an oven preheated to 400° C. The TEFLON taped wrapped assembly was then heated at sintering temperatures of 375° C. for four minutes, reversed, and then heated again at 375° C. for four minutes. The TEFLON taped assembly was then removed from the oven and the TEFLON tape and wire wraps were removed. The ePTFE grafts were then cut about one inch outside of each of the ends of the stents. Finally, the resulting encapsulated stents were gently removed from the mandrel one at a time and then cut to provide a 3 mm ePTFE overhang at both ends of the individual stents.

Figure 9:
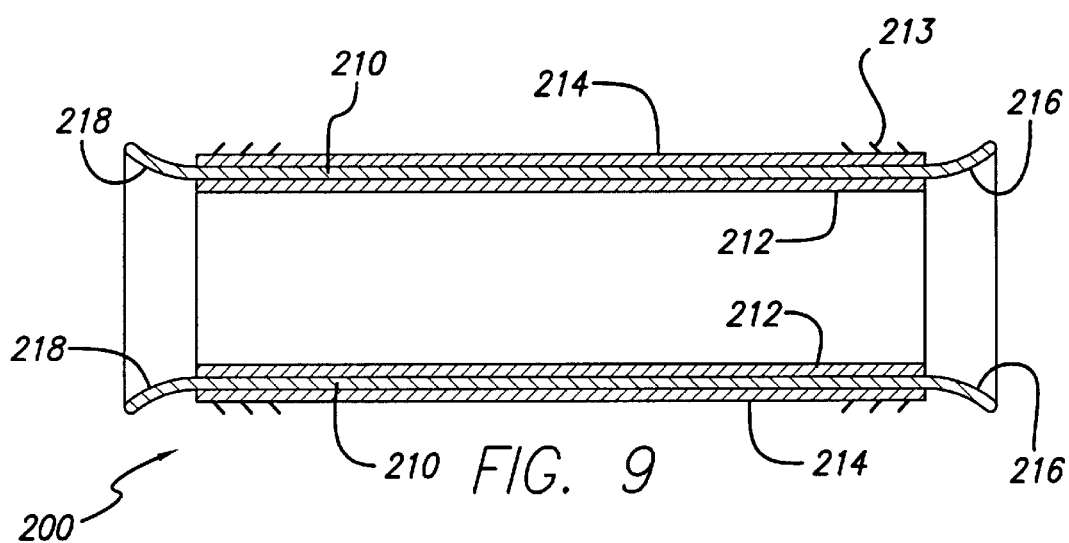
FIG. 9 is a longitudinal cross-sectional view of a radially enlarged encapsulated stent of the present invention illustrating exposed opposing ends of the tubular support member in their radially outwardly flared state as well as barbs that aid in the fixation of the device after expansion.

Finally, as illustrated in FIG. 9, there is provided a radially expanded encapsulated, stent 200 in accordance with the present invention. Radially expanded encapsulate stent 200 consists generally of a radially expandable tubular support member 210, which, as previously described consists of a radially expandable structure having a plurality of openings to accommodate radials expansion from a first diameter to a second radially enlarged diameter, and a first tubular member 212 and a second tubular member 214, each made of a biocompatible material, such as expanded polytetrafluoroethylene. The tubular support member 210 is interdisposed intermediate the first and second tubular members 212, 214, such that the first and second tubular members 212, 214 concentrically cover each of the abluminal and luminal surfaces of the tubular support member 210 and are radially expandable with the tubular support member 210 as previously described. Barbs 213 are formed in the second tubular member 214 and assist in fixation of the device after expansion. In accordance with this embodiment of the radially expanded encapsulated stent 200, however, opposing ends 216 and 218 of the radially expandable tubular support member 210 are exposed and uncovered by the first and second tubular members 212 and 214. Thus, during radial expansion of the radially and second tubular members 212 and 214. Thus, during radial expansion of the radially expandable encapsulated stent 200 from a first diameter to a second radially enlarged diameter, the opposing ends 216 and 218 offer less resistance to radial expansion than does the intermediate section of the tubular support member 210 which is covered by the first and second tubular members 212, 214, and the opposing ends 216, 218 tend to radially expand to a greater extent and flare radially outward and form flared projections which facilitate anchoring in the interluminal tissue.

Example 2

A 3 mm ID thin wall ePTFE graft was loaded onto a 3.56 mm mandrel. The top section of the 3 mm, ePTFE graft was wrapped with TEFLON tape to prevent migration. Next, three P-394 "PALMAZ" stents and three P-308 "PALMAZ" stents were pre-dilated on a 4.74 mm mandrel. The three P-394 pre-dilated stents were loaded first onto the 3 mm ePTFe graft, followed by the three P-308 pre-dilated stents, and then spaced equidistantly from another along the length of the 3 mm ePTFE graft. The predilated stents were then crimped onto the mandrel and a 4 mm ID ePTFE graft was loaded over the crimped stents. The 4 mm ePTFE graft was wire wrapped at both its ends and between the crimped stents. The entire assembly was then placed in an oven for 30 seconds and heated at 340° C. and then removed. The assembly was then wrapped tightly with TEFLON tape with the three P-308 stents being wrapped first. The entire TEFLON tape wrapped assembly was then heated at a sintering temperature of 375° C. for four minutes, reversed, and then heated at 375° C. for another four minutes in order to sinter the ePTFE grafts. The entire assembly was then removed and the TEFLON tape and wires were removed from the assembly. The grafts were then cut approximately one inch from the ends of each of the stents and the resulting encapsulated stents were gently removed from the mandrel one at a time. The ePTFE grafts were then cut to provide a 3 mm overhang at each end of the encapsulated stents.

The above-described examples formed encapsulated stents which appeared to comprise monolithic structures incapable of separation and delamination. Prior experiments produced structures having inner ePTFE graft layers which pulled away from the stent wall upon removal from the mandrel. This non-bonding problem was solved, as evidenced in the above-described examples, by using freshly expanded, ePTFE extrudate, compressing the first (inner) ePTFE graft onto the mandrel prior to loading the stents, and instituting a pre-warming step for the loaded assembly prior to applying pressure to the assembly by taping with TEFLON tape.

The ePTFE grafts preferably comprise initial internodal distances (INDs) within a range of 10 to 90 microns. Further, the inner and outer ePTFE grafts which comprise the radially expandable encapsulated stent may have difference INDs.

While the invention has been described with reference to preferred embodiments thereof, the description is for illustrative purposes only and is not to be construed as limiting the scope of the invention. Various modifications and changes may be made by those skilled in the art without departing from the true spirit of the scope of the invention as defined by the appended claims.

We claim:

1. A radially expandable reinforced vascular graft comprising:

a first and a second expanded polytetrafluoroethylene tubular member; and at least one radially expandable tubular shaped support member having a plurality of openings therein and interdisposed between the first and second tubular members, wherein the radially expandable tubular shaped support member has a length greater than the first and second tubular member lengths, wherein the second tubular member has barbs on the outer surface thereof, and wherein at least a portion of the first and second tubular members are adapted to pass into the plurality of openings in the support member and radially expand upon expansion of the support member.

2. A radially expandable reinforced vascular graft comprising:

a first and a second expanded polytetrafluoroethylene tubular member; and at least one radially expandable tubular shaped support member having a plurality of openings therein and interdisposed between the first and second tubular members, wherein the radially expandable tubular shaped support member has a length greater than the first and second tubular member lengths, forming funnel shaped ends upon expansion, and wherein at least a portion of the first and second tubular members are adapted to pass into the plurality of openings in the support member and radially expand upon expansion of the support member.

3. A radially expandable reinforced vascular graft comprising:

a first expanded polytetrafluoroethylene continuous tubular layer having a first internodal distance;

a second expanded polytetrafluoroethylene continuous tubular layer having a second internodal distance; and a radially expandable tubular support layer having a plurality of openings, said support layer being interdisposed between the first expanded polytetrafluoroethylene continuous tubular layer and the second expanded polytetrafluoroethylene continuous tubular layer, wherein the radially expandable tubular support layer has a length greater than a length of each of said first tubular layer and said second tubular layer.

\* \* \* \* \*